(12) United States Patent
Pettersson et al.

(10) Patent No.: US 11,674,264 B2
(45) Date of Patent: Jun. 13, 2023

(54) SYSTEM FOR TREATMENT OF A BIOMASS MATERIAL AND A METHOD FOR CONNECTING A VALVE TO A TRANSPORTING PIPE

(71) Applicant: VALMET AB, Sundsvall (SE)

(72) Inventors: Patrik Pettersson, Alnö (SE); Johan Carlsson, Alnö (SE); Peter Edlund, Sundsvall (SE)

(73) Assignee: VALMET AB, Sundsvall (SE)

( * ) Notice: Subject to any disclaimer, the term of this patent is extended or adjusted under 35 U.S.C. 154(b) by 209 days.

(21) Appl. No.: 17/055,302

(22) PCT Filed: Apr. 9, 2019

(86) PCT No.: PCT/SE2019/050328
§ 371 (c)(1),
(2) Date: Nov. 13, 2020

(87) PCT Pub. No.: WO2019/226087
PCT Pub. Date: Nov. 28, 2019

(65) Prior Publication Data
US 2021/0197155 A1 Jul. 1, 2021

(30) Foreign Application Priority Data

May 24, 2018 (SE) .................................. 1850625-3

(51) Int. Cl.
*D21B 1/36* (2006.01)
*D21C 1/02* (2006.01)
(Continued)

(52) U.S. Cl.
CPC ............. *D21B 1/36* (2013.01); *D21C 1/02* (2013.01); *D21C 7/08* (2013.01); *B01J 3/002* (2013.01);
(Continued)

(58) Field of Classification Search
None
See application file for complete search history.

(56) References Cited

U.S. PATENT DOCUMENTS 2,882,967 A * 4/1959 Surino .................... D21C 7/08
251/153
2009/0221814 A1 9/2009 Pschorn et al.

FOREIGN PATENT DOCUMENTS

EP 2725134 A1 4/2014
EP 3156539 A1 * 4/2017 ............... D21B 1/36
(Continued)

*Primary Examiner* — Jennifer A Leung
(74) *Attorney, Agent, or Firm* — Foley & Lardner LLP

(57) ABSTRACT

A system for treatment of a biomass material, said system comprising: a first vessel (3) in which said biomass material is treated under a first pressure; a second vessel (5) in which said biomass material is received and held at a second pressure which is lower than the first pressure; a transporting pipe (7) connecting an outlet (9) of the first vessel (3) with an inlet (11) of the second vessel (5) for transporting the biomass material from the first vessel to the second vessel; and a valve (15; 15'; 15) arranged in said transporting pipe (7), said valve being configured for controlling the flow of biomass material and fluid in the transporting pipe (7), wherein said transporting pipe (7) is asymmetrically connected to an outlet (33'; 33) of said valve (15; 15'; 15) such that a generated jet stream of biomass material delivered out from the outlet (33'; 33) of the valve (15; 15'; 15) is received closer to a transporting pipe longitudinal central axis (A1) than if the outlet (33'; 33) of the valve (15; 15'; 15) and the transporting pipe (7) would have been connected symmetrically.

20 Claims, 4 Drawing Sheets

(51) Int. Cl.
*D21C 7/08*    (2006.01)
*B01J 3/00*    (2006.01)
*B01J 3/03*    (2006.01)
*F16L 57/06*   (2006.01)
*B01J 3/02*    (2006.01)

(52) U.S. Cl.
CPC .. *B01J 3/02* (2013.01); *B01J 3/03* (2013.01); *C12P 2201/00* (2013.01); *F16L 57/06* (2013.01)

(56) References Cited

FOREIGN PATENT DOCUMENTS

| | | |
|---|---|---|
| WO | WO 2009/147512 A2 | 12/2009 |
| WO | WO 2015/199601 A1 | 12/2015 |
| WO | WO-2016171604 A1 * | 10/2016 ............... D21C 7/04 |

* cited by examiner

SYSTEM FOR TREATMENT OF A BIOMASS MATERIAL AND A METHOD FOR CONNECTING A VALVE TO A TRANSPORTING PIPE

TECHNICAL FIELD OF THE INVENTION

The present invention relates to a system for treatment of a biomass material and to a method in such a system.

BACKGROUND

Arrangements for pretreatment or prehydrolysis of biomass is known in the art. Such arrangement may comprise one or more pressurized reactors in which the biomass is pretreated with steam at elevated pressure and temperature with or without the addition of chemicals.

Temperature and time are two important parameters in such a prehydrolysis treatment. In particular, it is preferable that the desired temperature is reached as fast as possible in order to avoid building an excessively large reactor. It is furthermore important that the heating of the biomass is as homogenous as possible, since a heterogeneous heating may lead to unreacted, low-reacted or even over-reacted material, which in turn may cause yield loss, formation of undesired by-products and/or problems in the downstream process.

Typically, biomass material is treated with steam under pressure in a reactor and then transferred to a steam separation device, e.g. a cyclone, through a transporting pipe, often called a blow line. The cyclone can be pressurized or working at or below atmospheric pressure. However, the cyclone will be at a lower pressure than the reactor. A valve, often called a blow valve, is usually provided close to the outlet from the reactor in the blow line. Said blow valve is provided for controlling the flow through the transporting pipe. The blow valve will hereby provide a pressure drop to the biomass which is transported through the transporting pipe (blow line) from the reactor to the cyclone. There are several established ways of discharging material from pretreatments reactors, e.g. steam explosion (steam and moist particles in the flow) and dilution discharge (liquid and particles in the flow) or combinations of these two methods. The highest velocity in the blow line is typically obtained with a steam explosion discharge. Particles (biomass, sand or other impurities) which are travelling with high speed in the blow line will cause the blow line to erode. Erosion of the blow line (transporting pipe) is a big problem. Blow lines need to be changed or repaired frequently due to this. Especially directly after the blow valve there are often problems with erosion due to particles impinging the blow line surface unevenly, i.e. due to the valve construction. Particles will be distributed unevenly over the blow line circumference and particles will impinge certain points of the blow line surface more which will lead to erosion problems. At bends/elbows/junctions of the blow line the erosion problem is usually also big. A common way to handle these erosion problems is to minimize the number of bends, to have large radius on the bends or to use wear resistant liners in the bends and close to the blow valve.

SUMMARY

An object of the invention is to provide an improved system for the treatment of a biomass material.

A further object of the invention is to increase the life time of a transporting pipe provided in such a system.

This is achieved by a system and a method according to the independent claims.

According to one aspect of the invention a system is provided for treatment of a biomass material, said system comprising:
- a first vessel in which said biomass material is treated under a first pressure;
- a second vessel in which said biomass material is received and held at a second pressure which is lower than the first pressure;
- a transporting pipe connecting an outlet of the first vessel with an inlet of the second vessel for transporting the biomass material from the first vessel to the second vessel; and
- a valve arranged in said transporting pipe, said valve being configured for controlling the flow of biomass material and fluid in the transporting pipe, wherein said transporting pipe is asymmetrically connected to an outlet of said valve such that a generated jet stream of biomass material delivered out from the outlet of the valve is received closer to a transporting pipe longitudinal central axis, A1, than if the outlet of the valve and the transporting pipe would have been connected symmetrically.

According to another aspect of the invention a method for connecting a valve to a transporting pipe in a system for treatment of biomass material is provided. Said method comprises the steps of:
- determining a position in an outlet of a valve where a jet stream of biomass material is delivered out from the outlet;
- connecting a transporting pipe asymmetrically to the outlet of the valve in dependence of said determination.

Hereby, when a jet stream of biomass material is received closer to a transporting pipe longitudinal central axis the distribution of the flow into the transporting pipe will be more equal, i.e. there is less risk that particles are impinging at specific points thus leading to a quick erosion of the transporting pipe.

In one embodiment of the invention the asymmetrical connection of the transporting pipe to the outlet of the valve means that the transporting pipe longitudinal central axis is not aligned with a valve longitudinal central axis passing through a centre of the valve outlet.

In one embodiment of the invention said transporting pipe is asymmetrically connected to an outlet of said valve such that a generated jet stream of biomass material delivered out from the outlet of the valve is received substantially along the transporting pipe longitudinal central axis.

In one embodiment of the invention said valve comprises a flow channel part through which the biomass material is transported through the valve and a flow regulation part which can be moved for controlling the flow through the flow channel part, wherein the flow of biomass material is forced against a first side of an inner wall of the flow channel part by the flow regulation part. The forcing of the flow of biomass material towards the first side of the inner wall by the flow regulation part will cause a low-pressure zone to be built up directly after the flow regulation part towards a second side of the inner wall being opposite the first side. This low-pressure zone will cause jet streams of biomass material to be drawn towards the second side of the inner wall. After the jet stream has reached the second side of the inner wall of the flow channel part of the valve the jet stream is mostly following the inner wall out through the outlet of the valve and hereby a jet stream is leaving the valve close to a wall of the valve instead of from a position of a valve longitudinal central axis, A2, which is passing through a centre of the valve outlet. These types of valves which are delivering jet streams of material for example close to a wall of the valve are commonly used in this technical area and therefore the invention is useful in such systems for treatment of biomass material.

In one embodiment of the invention the outlet of the valve is connected to the transporting pipe such that a transporting pipe longitudinal central axis is provided between a valve longitudinal central axis and a second side of the inner wall of the flow channel part, said second side of the inner wall being an opposite side of the inner wall as compared to the first side of the inner wall.

In one embodiment of the invention the flow channel part of the valve comprises a wear part provided from the flow regulation part towards the outlet of the valve, wherein a length of said wear part is between 0.5-5 times the diameter of the flow channel part. Hereby the wear part is provided where jet streams, which are caused by the low-pressure zones built up directly after the flow regulation part, are impinging the second side of the inner wall.

In one embodiment of the invention the transporting pipe is connected to the valve such that the transporting pipe longitudinal central axis is provided substantially aligned with a second side of the inner wall of a flow channel part of the valve, said second side of the inner wall being opposite a first side of the inner wall of the flow channel part towards which the flow of biomass material is forced against by a flow regulation part of the valve. Hereby jet streams of biomass material which are leaving the outlet of the valve substantially along said second side of the inner wall of the valve will be received substantially along a transporting pipe longitudinal axis.

In one embodiment of the invention the valve is a piston valve where a flow regulation part of the valve is a piston forcing the flow of biomass material against a first side of an inner wall of a flow channel part by leaving a flow passage with controllable size between an outer end of the flow regulation part and the first side of the inner wall of the flow channel part.

In one embodiment of the invention the valve is a ball valve, a shutter valve or a throttle valve.

In one embodiment of the invention the first vessel is a reactor for pretreatment of a biomass material with steam or other heating media under a pressure of at least 5 bar (g) and a temperature of at least 130° C. and wherein the second vessel is a gas separation device.

In one embodiment of the invention the step of determining comprises measuring the flow of biomass material delivered out from the outlet of the valve at different positions of the outlet.

DETAILED DESCRIPTION OF EMBODIMENTS

As discussed above in the background chapter biomass material can be treated by steam at elevated pressure and temperature in a reactor as a step in a process for production of for example sugars, bioethanol, steam exploded pellets or various chemicals. The biomass material can be for example wood in different forms (wood chips, saw dust, splinters, etc), wheat straw, rice straw, bagasse, corn stover, empty fruit bunches, energy cane, different kinds of grass material or similar biomass materials.

Examples of treatment of biomass are auto or acid hydrolysis followed by steam explosion discharge, dilution discharge or combinations of these as described in the background. These methods differ by the content of liquid/water in the biomass material.

Figure 1:
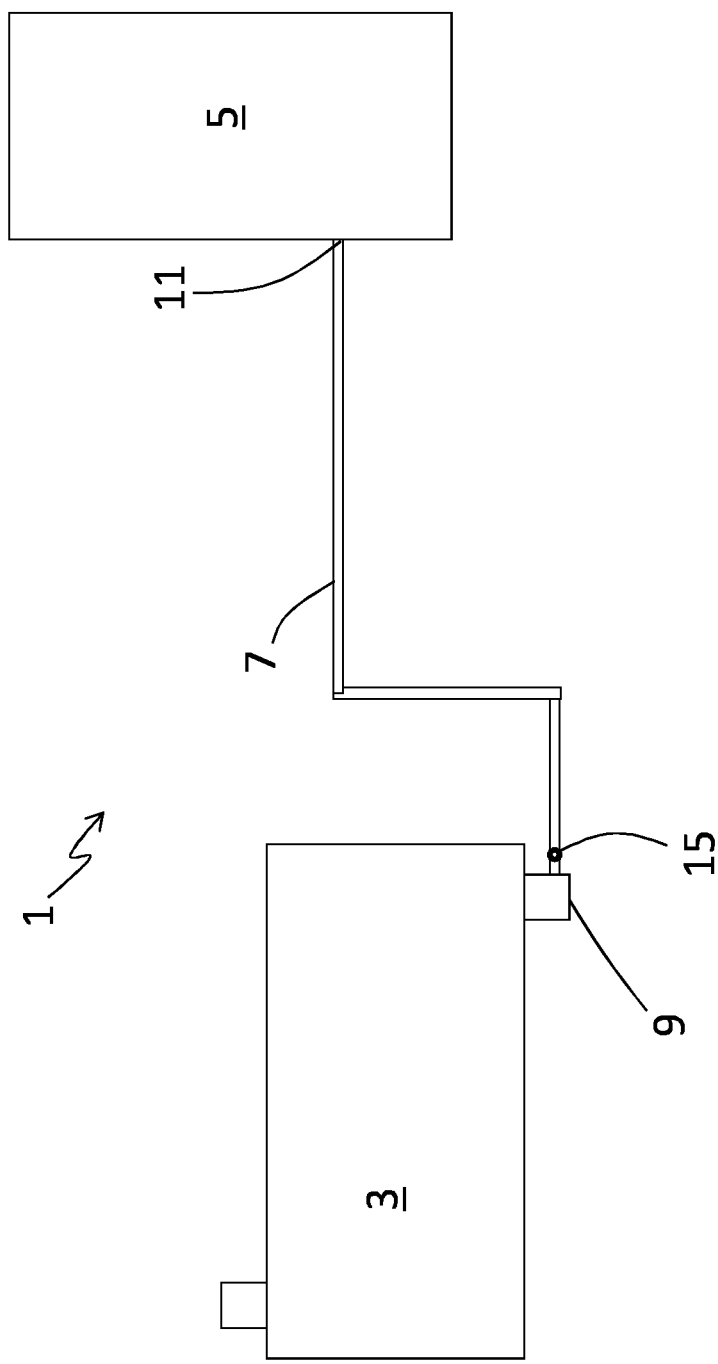
FIG. 1 shows schematically a system for treatment of a biomass material according to one embodiment of the invention.

In FIG. 1 a system 1 for treatment of a biomass material according to one embodiment of the invention is shown schematically. Said system comprises a first vessel 3 in which said biomass material is treated at a first pressure. Said first vessel can for example be a reactor or a refiner and can be used for pretreatment of biomass material at elevated pressure and temperature for example by steam. If the first vessel is a refiner, it is usually connected to a reactor at an inlet of the refiner. The first vessel can comprise a discharger provided at an outlet of the first vessel. The pressure in the first vessel can typically be in the range 5-30 bar (g), but significantly higher pressures are also used in these systems. The temperature in the first vessel can typically be in the range of 130-250° C. The system comprises further a second vessel 5 in which said biomass material is collected at a second pressure which is lower than the first pressure. The second vessel can be a separation device, such as a gas separation device which is separating gas from solids and/or liquid, e.g. a cyclone or a mechanical separator. The second vessel 5 can be a pressurized vessel or at atmospheric pressure. The system 1 comprises furthermore a transporting pipe 7 connecting an outlet 9 of the first vessel 3 with an inlet 11 of the second vessel 5 for transporting the biomass material from the first vessel 3 to the second vessel 5.

Usually a valve 15, often called a blow valve 15, is provided in the transporting pipe 7 (often called a blow line) close to the outlet 9 from the first vessel 3. The blow valve 15 is provided for controlling the flow of biomass material and steam in the transporting pipe 7.

Commonly used blow valves in these types of systems are for example ball valves, shutter valves and piston valves, which valves force the flow of biomass material towards one side of a flow channel of the valve. An example of such a valve is EvoThrottle™ from Valmet. This non-symmetric distribution of the flow inside a flow channel of the valve will cause erosion problems as will be further described below in relation to FIGS. 2a and 2b.

Figure 2A:
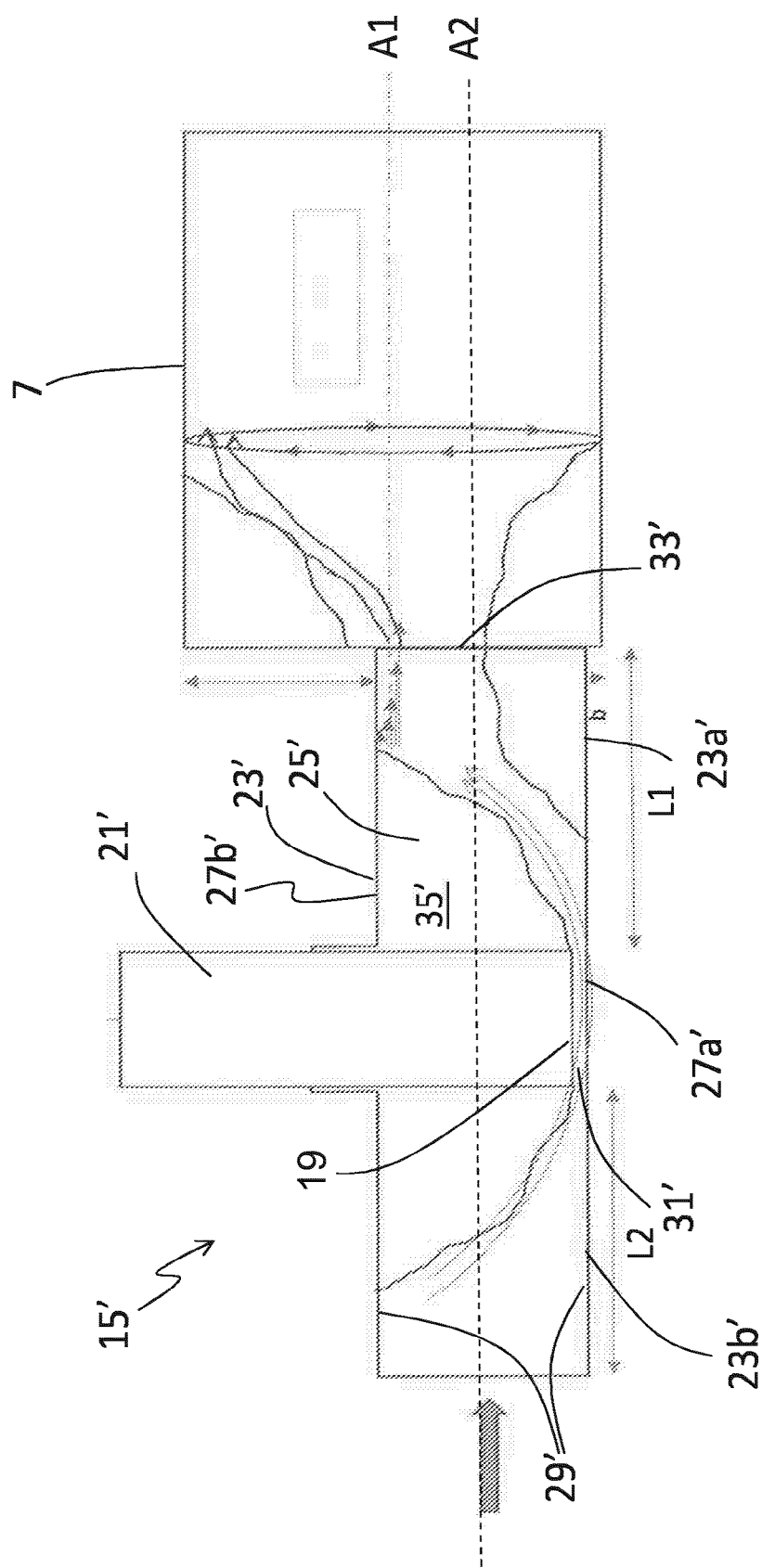
FIG. 2a is a schematic drawing of a valve connected to a transporting pipe according to one embodiment of the invention.

FIG. 2a is a schematic drawing of a valve 15' connected to a transporting pipe 7 according to one embodiment of the invention. This valve 15' is a type of piston valve comprising a flow regulation part 21' in the form of a piston 21' and a flow channel part 23'. The flow channel part 23' comprises a flow channel 25' having for example a circular cross section or a rectangular or quadratic cross section. The flow regulation part 21' will force the flow of biomass material against a first side 27a' of an inner wall 29' of the flow channel part 23'. The flow regulation part 21' protrudes into the flow channel 25' through a second side 27b' of the inner wall 29' of the flow channel part 23'. Said second side 27b' being opposite the first side 27a'. A geometry of the flow channel part 23' may be adapted to the geometry of the flow regulation part 21' where the flow regulation part 21' is provided such that it fits and seals properly. For example, if the flow channel has a circular cross section and the flow regulation part 21' has a quadratic cross section the flow channel will be made quadratic where the flow regulation part 21' is provided. A flow passage 31' is hereby provided between an outermost end 19 of the flow regulation part 21' and the first side 27a' of the inner wall 29' of the flow channel part 23'. The size of this flow passage is controllable by moving the flow regulation part 21'.

Furthermore, the flow channel part 23' comprises a first elongated flow channel part 23a' between the position of the flow regulation part 21' and an outlet 33' of the valve 15'. This elongated flow channel part 23a' is also called a wear part 23a' and comprises a wear resistance material or a wear lining in order to resist erosion produced by a jet stream of biomass material which will impinge on the second side 27b' of the inner wall 29' a certain distance after the flow regulation part 21' in a direction towards the outlet 33' of the valve 15'. The forcing of the flow of biomass material towards the first side 27a' of the inner wall 29' by the flow regulation part 21' will cause a low-pressure zone 35' to be built up directly after the flow regulation part 21' towards the second side 27b' of the inner wall 29'. This low-pressure zone 35' will cause jet streams of biomass material to be drawn towards the second side 27b' of the inner wall 29'. Hereby the elongated flow channel part 23a' is suitably provided with a wear resistant material. A length of the first elongated flow channel part 23a', L1, can be for example 0.5-5 times the diameter of the flow channel part. In the embodiment of the invention as schematically shown in FIG. 2a a second elongated flow channel part 23b' is provided on the other side of the flow regulation part 21'. A length of the second elongated flow channel part 23b', L2, does however not need to be as long as the length, L1, of the first elongated flow channel part 23a'.

After the jet stream has reached the second side 27b' of the inner wall 29' of the flow channel part 23' of the valve 15' the jet stream is mostly following the inner wall 29' out through the outlet 33' of the valve 15' and hereby a jet stream is leaving the valve close to a wall of the valve instead of from a position of a valve longitudinal central axis, A2, which is passing through a centre of the valve outlet 33'.

Figure 2B:
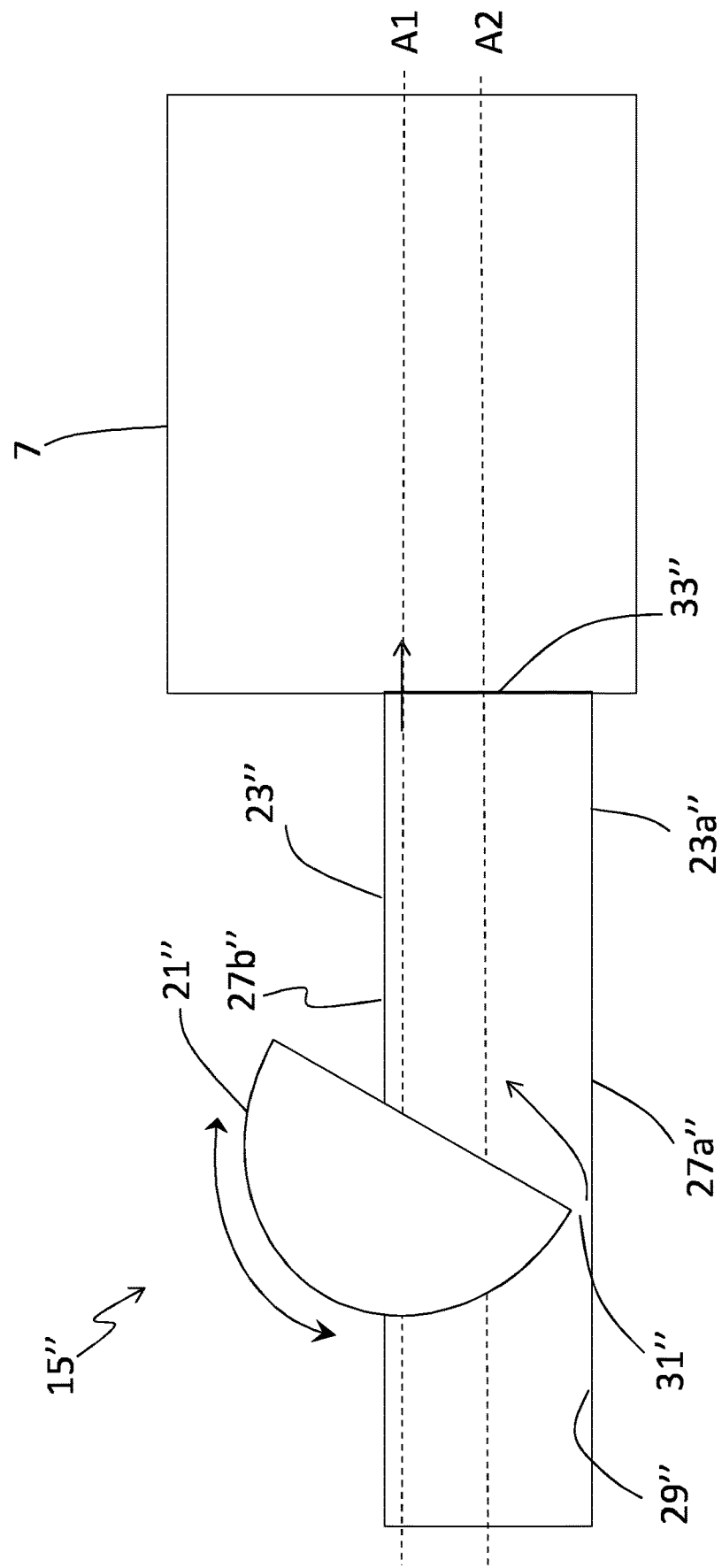
FIG. 2b is a schematic drawing of a valve connected to a transporting pipe according to another embodiment of the invention.

FIG. 2b is a schematic drawing of a valve 15" connected to a transporting pipe 7 according to another embodiment of the invention. In this embodiment the valve 15" is a ball valve instead of a piston valve as described in relation to FIG. 2a. Many details are similar to the details of the embodiment as described in relation to FIG. 2a and will not be described again. The difference in this embodiment is that the flow regulation part 21" is a ball instead of a piston. A flow passage 31" is provided between the flow regulation part 21" and a first side 27a" of the inner wall 29" of the flow channel part 23". The size of the flow passage 31" is controlled by rotating the flow regulation part 21". The biomass material will be forced against the first side 27a" of the inner wall 29" and a jet stream of biomass material will after the flow regulation part 21" be directed towards a second side 27b" of the inner wall 29" of the flow channel part 23" in the same way as described in relation to FIG. 2a. A first elongated flow channel part 23a" comprising a wear resistant material is provided with the same example dimensions as mentioned in relation to FIG. 2a. After the jet stream has reached the second side 27b" of the inner wall 29" of the flow channel part 23" of the valve 15" the jet stream is mostly following the inner wall 29" out through the outlet 33" of the valve 15" and hereby a jet stream is leaving the valve close to a wall of the valve instead of from a position of a valve longitudinal central axis, A2, which is passing through a centre of the valve outlet 33".

The inventive idea will now be described with reference to both embodiments as shown in FIGS. 2a and 2b.

According to the invention said transporting pipe 7 is asymmetrically connected to the outlet 33'; 33" of said valve 15'; 15" such that a jet stream of biomass material delivered out from the outlet 33'; 33" of the valve 15'; 15" is received closer to a transporting pipe longitudinal central axis, A1, than if the outlet 33'; 33" of the valve 15'; 15" and the transporting pipe 7 would have been connected symmetrically.

The asymmetrical connection of the transporting pipe 7 to the outlet 33'; 33" of the valve 15'; 15" means that the transporting pipe longitudinal central axis, A1, is not aligned with a valve longitudinal central axis, A2, which is passing through a centre of the valve outlet 33'; 33'. This could also be explained as the transporting pipe 7 being connected to the outlet 33'; 33" of said valve 15; 15'; 15" with an offset.

In one embodiment of the invention said transporting pipe 7 is asymmetrically connected to the outlet 33'; 33" of said valve 15'; 15" such that a jet stream of biomass material delivered out from the outlet 33'; 33" of the valve is received substantially along the transporting pipe longitudinal central axis, A1. Depending on the dimensions of the valve 15 and transporting pipe 7 this may be difficult to achieve. However, the transporting pipe 7 can be connected to the valve 15 with an offset, i.e. with regard to their respective longitudinal central axes, A1, A2, such that the transporting pipe longitudinal central axis, A1, is provided as close as possible to where a jet stream of biomass material mainly is delivered out from the valve outlet 33'; 33". This may be close to one side of the inner wall 29'; 29" of the flow channel part 23'; 23". In one embodiment of the invention measurements are performed for determining where a jet stream is delivered out from the outlet of the valve. Thereafter the transporting pipe 7 is connected to the valve 15 in accordance with these measurements. This is further described in relation to FIG. 3.

In one embodiment of the invention the outlet 33'; 33" of the valve 15'; 15" is connected to the transporting pipe 7 such that a transporting pipe longitudinal central axis, A1, is provided between a valve longitudinal central axis, A2, and the second side 27b'; 27b" of the inner wall 29'; 29" of the flow channel part 23'; 23".

In one embodiment of the invention the transporting pipe 7 is connected to the valve 15'; 15" such that the transporting pipe longitudinal central axis, A1, is provided substantially aligned with the second side 27b'; 27b" of the inner wall 29'; 29" of a flow channel part 23'; 23" of the valve 15'; 15". Said second side 27b'; 27b" of the inner wall 29'; 29" is opposite the first side 27a'; 27a" of the inner wall 29'; 29" of the flow channel part towards which the flow of biomass material is forced against by the flow regulation part 21'; 21" of the valve. The jet stream of biomass material will after impinging at the second side 27b'; 27b" of the flow channel part 23'; 23" mainly protrude along the wall surface 29'; 29" of the flow channel part 23'; 23". Hereby the jet stream of biomass material will often be delivered out from the outlet 33'; 33" of the valve 15'; 15" along the wall and therefore it is a convenient embodiment of the invention to position the transporting pipe 7 with this relationship.

Figure 3:
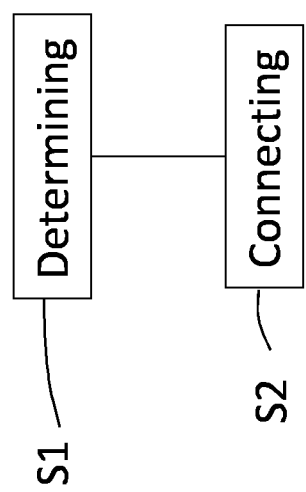
FIG. 3 is a flow chart of a method according to one embodiment of the invention.

A method for connecting a valve 15 to a transporting pipe 7 in a system for treatment of biomass material as described above in relation to FIG. 1 is also provided according to the invention. A flow chart of the method is shown in FIG. 3. Said method comprises the steps of:

S1: Determining a position in an outlet (33'; 33") of a valve (15; 15'; 15") where a jet stream of biomass material leaves the outlet.

S2: Connecting a transporting pipe (7) asymmetrically to the outlet (33'; 33") of the valve in dependence of said determination in step S1 such that a generated jet stream of biomass material delivered out from the outlet (33'; 33") of the valve (15; 15'; 15") is received closer to a transporting pipe longitudinal central axis (A1) than if the outlet (33'; 33") of the valve (15; 15'; 15") and the transporting pipe (7) would have been connected symmetrically.

In one embodiment of the invention said determining comprises measuring the flow of biomass material delivered out from the outlet of the valve at different positions of the outlet.

Asymmetrically connecting means that the transporting pipe longitudinal central axis, A1, is not aligned with a valve longitudinal central axis, A2, which is passing through a centre of the valve outlet 33'; 33'. Further details around different examples of positioning of the transporting pipe 7 in relation to the valve 15 is given in the description above in relation to FIGS. 2a and 2b.

The invention claimed is:

1. A system for treatment of a biomass material, the system comprising:
   a first vessel configured for treating the biomass material under a first pressure;
   a second vessel configured for receiving the biomass material and holding the biomass material at a second pressure which is lower than the first pressure;
   a transporting pipe connecting an outlet of the first vessel with an inlet of the second vessel, and configured for transporting the biomass material from the first vessel to the second vessel; and
   a valve arranged in the transporting pipe, the valve being configured to control a flow of the biomass material in the transporting pipe;
   wherein the transporting pipe is asymmetrically connected to an outlet of the valve such that a generated jet stream of the biomass material delivered out from the outlet of the valve is received closer to a transporting pipe longitudinal central axis than if the outlet of the valve and the transporting pipe would have been connected symmetrically.

2. The system of claim 1, wherein the asymmetrical connection of the transporting pipe to the outlet of the valve results in the transporting pipe longitudinal central axis being not aligned with a valve longitudinal central axis passing through a center of the outlet of the valve.

3. The system of claim 1, wherein the transporting pipe is asymmetrically connected to the outlet of the valve such that the generated jet stream is received substantially along the transporting pipe longitudinal central axis.

4. The system of claim 1, wherein:
   the valve comprises:
      a flow channel part through which the biomass material is transported through the valve, and
      a flow regulation part which can be moved for controlling the flow through the flow channel part; and
   the flow is forced against a first side of an inner wall of the flow channel part by the flow regulation part.

5. The system of claim 4, wherein the outlet of the valve is connected to the transporting pipe such that the transporting pipe longitudinal central axis is provided between a valve longitudinal central axis and a second side of the inner wall of the flow channel part, the second side of the inner wall being an opposite side of the inner wall as compared to the first side of the inner wall.

6. The system of claim 4, wherein:
   the flow channel part comprises a wear part provided from the flow regulation part towards the outlet of the valve; and
   a length of the wear part is between 0.5 and 5 times a diameter of the flow channel part.

7. The system of claim 1, wherein the transporting pipe is connected to the valve such that the transporting pipe longitudinal central axis is substantially aligned with a second side of an inner wall of a flow channel part of the valve, the second side of the inner wall being opposite a first side of the inner wall of the flow channel part towards which the flow of the biomass material is forced against by a flow regulation part of the valve.

8. The system of claim 1, wherein the valve is a piston valve where a flow regulation part of the valve is a piston forcing the flow of the biomass material against a first side of an inner wall of a flow channel part by leaving a flow passage with controllable size between an outer end of the flow regulation part and the first side of the inner wall of the flow channel part.

9. The system of claim 1, wherein the valve is a ball valve, a shutter valve, or a throttle valve.

10. The system of claim 1, wherein:
    the first vessel is configured for treating the biomass material with steam or other heating media where the first pressure is at least 5 bar (g) and at a temperature of at least 130° C.; and
    the second vessel is a gas separation device.

11. A method comprising:
    determining a position in an outlet of a valve where a jet stream of a biomass material is delivered out from the outlet; and
    connecting a transporting pipe asymmetrically to the outlet based on the determination such that the jet stream is received closer to a transporting pipe longitudinal central axis than if the outlet and the transporting pipe would have been connected symmetrically.

12. The method of claim 11, wherein determining the position comprises measuring a flow of the biomass material delivered out from the outlet at different positions of the outlet.

13. A system for treatment of a biomass material, the system comprising:
    a first vessel configured for treating the biomass material under a first pressure;
    a second vessel configured for receiving the biomass material and holding the biomass material at a second pressure which is lower than the first pressure;
    a transporting pipe connecting an outlet of the first vessel with an inlet of the second vessel and configured for transporting the biomass material from the first vessel to the second vessel; and
    a valve having an outlet connected to the transporting pipe, the valve being configured to control a flow of the biomass material in the transporting pipe, wherein the valve comprises:
       a flow channel part configured for transporting the biomass material through the valve, the flow channel part having an inner wall with a first side and a second side opposite the first side, and
       a flow regulation part configured to be moved in a direction between the first side and the second side to control the flow of the biomass material through the flow channel part, wherein a transporting pipe longitudinal central axis of the transporting pipe is offset from a valve longitudinal central axis of the valve such that the transporting pipe longitudinal central axis is between the valve longitudinal central axis and the second side of the inner wall of the flow channel part.

14. The system of claim 13, wherein the asymmetrical connection of the transporting pipe to the outlet of the valve results in the transporting pipe longitudinal central axis being not aligned with the valve longitudinal central axis passing through a center of the outlet of the valve.

15. The system of claim 13, wherein the transporting pipe is asymmetrically connected to the outlet of the valve such that the generated jet stream is received substantially along the transporting pipe longitudinal central axis.

16. The system of claim 13, wherein the valve is a piston valve.

17. The system of claim 13, wherein:
the flow channel part comprises a wear part provided from the flow regulation part towards the outlet of the valve; and
a length of the wear part is between 0.5 and 5 times a diameter of the flow channel part.

18. The system of claim 13, wherein the valve is a ball valve, a shutter valve, or a throttle valve.

19. The system of claim 13, wherein:
the first vessel is configured for treating of the biomass material with steam or other heating media where the first pressure is at least 5 bar (g) and at a temperature of at least 130° C.; and
the second vessel is a gas separation device.

20. A method for treatment of a biomass material, the method comprising:
providing a system comprising:
a first vessel configured for treating the biomass material under a first pressure,
a second vessel configured for receiving and holding the biomass material at a second pressure which is lower than the first pressure,
a transporting pipe connecting an outlet of the first vessel with an inlet of the second vessel, and
a valve having an outlet connected to the transporting pipe, the valve being configured to control a flow of the biomass material in the transporting pipe, wherein the valve comprises:
a flow channel part configured for transporting the biomass material through the valve, the flow channel part having an inner wall with a first side and a second side opposite the first side, and
a flow regulation part configured to be moved for controlling the flow through the flow channel part,
wherein a longitudinal central axis of the transporting pipe is offset from a longitudinal central axis of the valve such that the longitudinal central axis of the transporting pipe is between the longitudinal central axis of the valve and the second side of the inner wall of the flow channel part; and
transporting the biomass material from the first vessel to the second vessel via the valve and the transporting pipe such that the biomass material is forced by the flow regulation part to flow against the first side of the inner wall of the flow channel part, is then caused to flow in a jet stream so as to contact the second side of the inner wall opposite the first side, and then follows the second side of the inner wall until exiting the outlet of the valve.

* * * * *